United States Patent [19]
Jelko et al.

[11] Patent Number: 5,869,736
[45] Date of Patent: Feb. 9, 1999

[54] OXIDATION IN THE WITTEN-HERCULES PROCESS FOR PREPARING DIMETHYL TEREPHTHALATE

[75] Inventors: Stefan Jelko, Haltern; Anton Schoengen, Witten; Hermann-Josef Korte, Haltern; Gerhard Franz, Marl; Hans-Guenther Srebny, Nienburg; Thomas Jostmann, Duelmen; Frank Steding, Marl, all of Germany

[73] Assignee: Huels Aktiengesellschaft, Marl, Germany

[21] Appl. No.: 949,336

[22] Filed: Oct. 14, 1997

[30] Foreign Application Priority Data

Oct. 11, 1996 [DE] Germany .................. 196 41 912.3

[51] Int. Cl.$^6$ .................................................. C07C 67/00
[52] U.S. Cl. ................................................ 560/77
[58] Field of Search .................................. 560/77

[56] References Cited

U.S. PATENT DOCUMENTS 3,914,287 10/1975 Takeda et al. ............................. 560/77

*Primary Examiner*—Paul J. Killos
*Assistant Examiner*—Jafar Parsa

*Attorney, Agent, or Firm*—Oblon, Spivak, McClelland, Maier & Neustadt, P.C.

[57] ABSTRACT

A process is provided for the oxidation of p-xylene and methyl p-tolulate with oxygen-containing gases in the Witten-Hercules process for preparing dimetyl terephthalate in at least two sequentially arranged stages and in the presence of a catalyst, wherein the process involves oxidizing p-xylene and methyl p-toluate with oxygen containing gases in at least two sequential stages in the presence of a catalyst, wherein the at least two sequential stages include at least one p-xylene rich stage and at least one methyl p-toluate rich stage, wherein at least one of the following steps (a) and (b) occurs:

(a) in the at least one p-xylene rich stage at least a portion of p-xylene present is oxidized in the presence of 5 to 30% by mass of methyl p-toluate, based on a total amount of oxidation mixture in the at least one p-xylene rich stage; or (b) in the methyl p-toluate rich stage at least one of methyl p-toluate or p-toluic acid is oxidized in the presence of 2 to 30% by mass of p-xylene, based on a total amount of methyl p-toluate and p-toluic acid in the methyl p-toluate rich stage.

15 Claims, 2 Drawing Sheets

OXIDATION IN THE WITTEN-HERCULES PROCESS FOR PREPARING DIMETHYL TEREPHTHALATE

BACKGROUND OF THE INVENTION

1. Field of the Invention

The present invention relates to an improved oxidation procedure in the Witten-Hercules process for preparing dimethyl terephthalate (DMT).

2. Disccusion of the Background

In the Witten-Hercules process for preparing DMT, p-xylene (pX) is oxidized in one or more stages with oxygen-containing gases, such as air, in the presence of cobalt catalysts and manganese catalysts to give p-toluic acid (pTA). The pTA is then esterified with methanol to give methyl p-toluate (pTE), which is recycled to the oxidation, where it is oxidized to give terephthalic acid monomethylester (monomethyl terephthlate; MMT). The oxidation product pTA still has one further oxidizable methyl group and is therefore oxidized to terephthalic acid (TPA) like pTE to MMT under very similar conditions. However, since the melting temperature of pTA is higher than the oxidation temperature and the resulting TPA cannot be melted and is poorly soluble in the reaction medium, this reaction may only take place to a restricted extent, since the oxidized product can otherwise no longer be handled. It is therefore characteristic of all embodiments of the Witten-Hercules process that pTE is oxidized in a competing reaction to MMT. MMT is considerably more soluble than TPA, and pTE is a good solvent for pTA and MMT, has a low melting point and, even in relatively low amounts, considerably depresses the melting temperature of the oxidized product.

A comparable action is exerted by recirculated products which originate from subsequent stages of the DMT process. In addition to the highly predominant contents of substances neutral to oxidation, such as methyl benzoate (BME), DMT, dimethyl o-phthalate (DMO) and dimethyl isophthalate (DMI), the recirculated products have minor amounts of oxidizable contents, such as methyl terephthalaldehydrate (TAE) and methyl hydroxymethylbenzoate (HMBME). Particularly active compounds in this context are DME, DMT and DMI. If these recirculated products are introduced into the oxidation of pX, the amount of pTE also introduced can be kept lower. This is desirable, because separating off excess, (i.e. unoxidized), pTE in the work-up distillation stage following oxidation and esterification (the so-called crude ester distillation) requires high energy consumption. The high content of the substances neutral to oxidation in the recirculated products is therefore accepted as a lesser evil, although they decrease the space-time yield and require an elevation in reaction temperature. Obviously, in plants having only low amounts of recirculated products, as described in DE-A-39 04 586, correspondingly higher amounts of pTE have to be conducted to the pX oxidation.

In the esterification stage, which follows oxidation, MMT and TPA, as well as pTA, are esterified with methanol, and the crude ester mixture, having DMT and pTE as major constituents, is separated by distillation. The crude DMT can be purified by further distillation and/or crystallization. From DMT, pure terephthalic acid (commercial designation PTA) which can be directly esterified with glycols, can also be produced by hydrolysis. It is characteristic of the Witten-Hercules process that pX and pTE in the mixture are oxidized and that pTA, TPA and MMT are esterified jointly.

Whereas the oxidation of pX to pTA is associated with only low yield losses, the oxidation of pTE to MMT or of pTA to TPA is the greatest source of loss in the process. This applies at least if, according to a conventional mode of operation, all of the pX and all of the pTE and, if desired, the above-noted recirculated products are fed to the start of the oxidation zone and are allowed to flow jointly together with the catalyst through the entire single- or multi-stage oxidation zone, in which they are oxidized to the desired degree of conversion, with or without multiple addition of fresh air.

The oxidation of pX to pTA proceeds at a considerably higher rate than the oxidation of pTE to MMT or of pTA to TPA. Therefore, at the beginning of the oxidation at moderate temperatures, such as 140° to 145° C., by far the greatest portion of the pX is first oxidized. There are narrow limits for the choice of oxidation temperature. Below 135° C., the conversion rates decrease greatly, the reaction terminates readily and there are considerable safety risks because of possible oxygen break-throughs, with the explosion limit exceeded. Furthermore, at such low temperatures in the cooling systems of the oxidizers, only low-pressure steam can be generated, which is of restricted utility. Temperatures >150° C. are likewise disadvantageous, since at the customary reaction pressures of 6 to 8 bar, much pX and pTE are discharged with the off-gas and must be recovered. Additionally, at such elevated temperatures the oxygen is consumed so rapidly that the concentration falls below the desired oxygen concentration in the off-gas of at least 2%. Oxygen deficiency in the reaction mixture leads to increased formation of high-boilers, such as bi- and terphenyls, whereas high temperatures and excess oxygen promote total oxidation. Bi- and terphenyls constitute losses, since they cannot be converted into materials of value.

The oxidation of pTE and/or pTA to a significant extent does not succeed until the pX is substantially oxidized and, in addition, the temperature is increased by 10° to 25° C. The temperature must be further increased by approximately 10° C. if, as done conventionally, the above-noted recirculated streams are introduced into the initial region of the oxidation zone together with pTE, or simultaneously with pTE. The losses due to total oxidation and formation of high-boilers then increase considerably. However, such temperatures are currently unavoidable in practice if satisfactory conversion rates are to be achieved.

In its simplest embodiment, the oxidation stage of the Witten-Hercules process operates batchwise. pX and pTE are introduced together with catalyst solution, the mixture is heated and air is introduced until the desired degree of oxidation is achieved. In the simplest continuous embodiment, pX, pTE, air and catalyst solution are fed to a single oxidizer and the oxidation mixture is continuously taken off. This embodiment operates at a defined preset temperature, and therefore does not take into account the requirements resulting from the differences in oxidation properties mentioned of the different constituents of the oxidation mixture.

A variant of the single-stage oxidation is described in JA-B2 62/14537. Its process provides two oxidation columns arranged in parallel, of which one is charged with a molar excess of pX and the other with a molar excess of pTE. The temperatures in the two parallel oxidizers can be the same or different and are preferably 150° to 190° C. This arrangement improves the yield of DMT versus the single oxidizer process. However, the publication does not give any teaching on the relationship between the composition of the oxidation mixture in the two oxidizers and the optimum temperature; and no temperatures are specified in the examples. Furthermore, the preferred temperature range is so high that total oxidation and formation of high-boilers occur to a considerable extent, as is also shown by the unsatisfactory yields in the tables accompanying the examples.

The most usual arrangement of oxidizers in continuous processes is that of two, or preferably three, oxidizers arranged in series (i.e., sequentially). In this arrangement the temperature in the individual oxidizers can be readily matched to the particular composition of the oxidation mixture and to other operating circumstances. It is widely common to conduct all of the pX and all of the pTE, with or without all of the recirculated products, through the entire oxidation stage which is divided by the oxidizers into part-stages.

BRIEF DESCRIPTION OF THE DRAWINGS

Various other objects, features and attendant advantages of the present invention will be more fully appreciated as the same becomes better understood from the following detailed description when considered in connection with the accompanying figures wherein.

SUMMARY OF THE INVENTION

Figure 1:
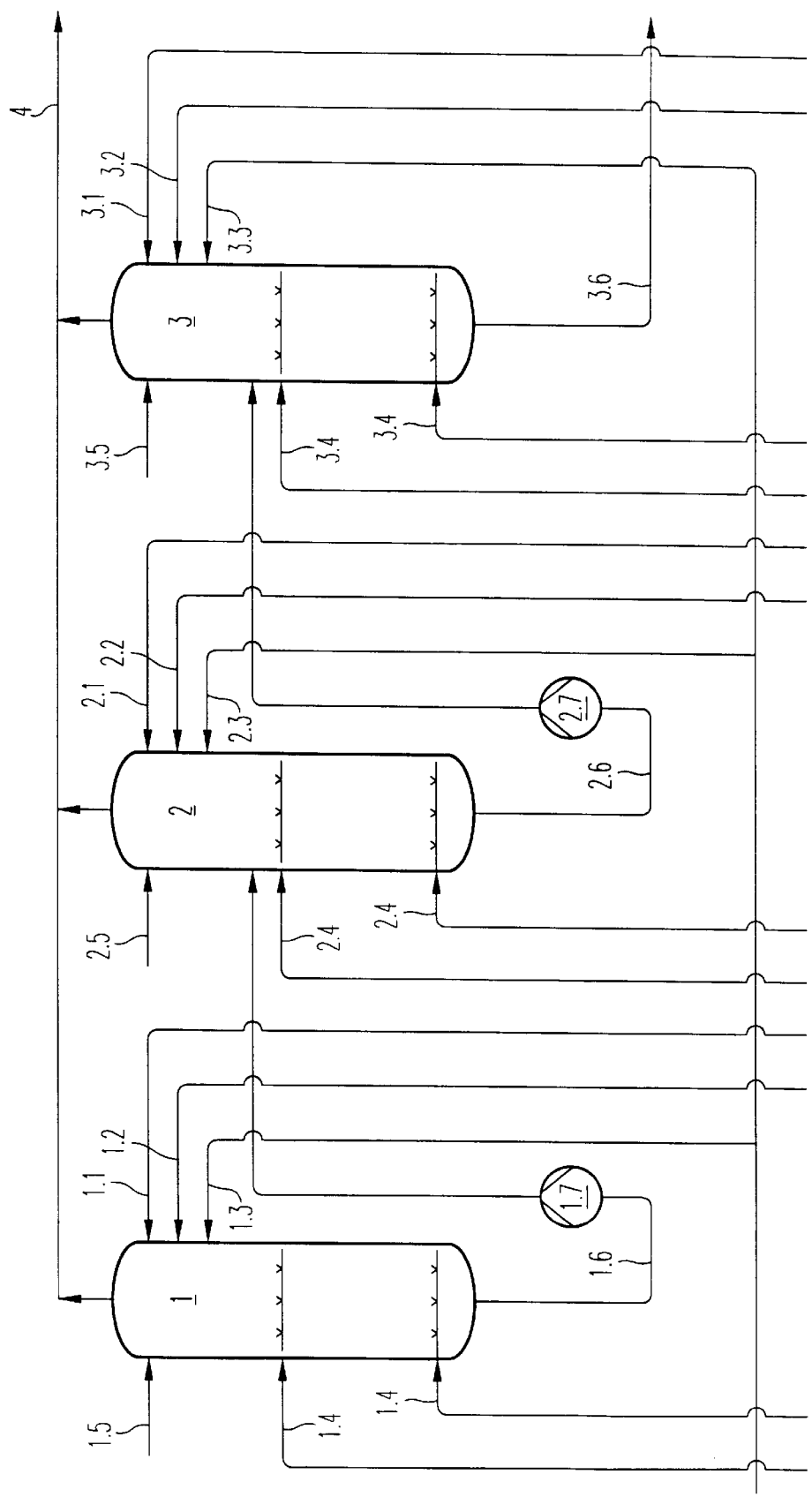
FIG. 1 is a diagram of a three-stage plant which has three oxidizers arranged in series and in which the process according to the present invention can be carried out.

Accordingly, one object of the present invention is to provide a process for preparing DMT that is more selective for DMT production and gives higher DMT yields.

This and other objects of the present invention have been satisfied by the discovery of a process for oxidation of pX and pTE, particularly in the preparation of DMT, comprising oxidizing p-xylene and methyl p-toluate with oxygen containing gases in at least two sequential stages in the presence of a catalyst, wherein said at least two sequential stages comprise at least one p-xylene rich stage and at least one methyl p-toluate rich stage, wherein at least one of the following steps (a) and (b) occurs: (a) in said at least one p-xylene rich stage at least a portion of p-xylene present is oxidized in the presence of 5 to 30% by mass of methyl p-toluate, based on the total amount of oxidation mixture in said at least one p-xylene rich stage or (b) in said methyl p-toluate rich stage at least one of methyl p-toluate or p-toluic acid is oxidized in the presence of 2 to 30% by mass of p-xylene, based on a total amount of methyl p-toluate and p-toluic acid in said methyl p-toluate rich stage.

DETAILED DESCRIPTION OF THE PREFERRED EMBODIMENTS

It has been found that the stage of catalytic oxidation of pX and pTE with oxygen-containing gases in the Witten-Hercules process for preparing DMT in at least two sequentially arranged stages (hereinafter called "sequential stages") and in the presence of a catalyst can be made more selective and the yield of DMT may be improved if at least one of the following (a) and (b) are met: (a) in at least one pX-rich stage, some of the pX and, if appropriate, recirculated products having oxidizable contents from later stages of the DMT process, are oxidized in the presence of 5 to 30% by mass of pTE, based on the total amount of reaction mixture in the pX-rich stage, or (b) in at least one pTE-rich stage pTE and/or pTA and, if appropriate, recirculated products are oxidized in the presence of 2 to 30% by mass of pX, based on the total amount of pTE and pTA in the pTE rich stage.

It has been found that it is advantageous to oxidize pX in the presence of a restricted amount of pTE and to ensure the presence of a defined minimum amount of pX during the oxidation of pTE and pTA. It has in fact been found that pX is an effective H donor, which is believed to counteract the decomposition of peroxy radicals formed as intermediates and thus counteract the undesirable processes of total oxidation and formation of high-boilers. The terms "pX-rich stage" and "pTE-rich stage" are not intended as statements of the absolute concentrations of pX and pTE in the respective stage, but to indicate that in each case one of the two substances is present in an amount which dominates over the other in accordance with the above conditions (a) and (b). Furthermore, the statement that pX is oxidized in at least one stage and pTE is oxidized in at least one stage is not to be taken to mean that the other substance in each case in the relevant stage was neutral to oxidation. Obviously, in both stages both substances are oxidized, but predominantly pX in the pX-rich stage, and predominantly pTE in the pTE-rich stage.

The process according to the present invention achieves a number of surprising advantages:

(1) The selectivity of the pX oxidation is increased by several percentage points. pX is believed to act as a stabilizing H donor even when oxidation is carried out in the pTE-rich stage at the concentrations according to the invention and the lower temperatures of <160° C. which are then possible. Furthermore, if recirculated products are not introduced into the first part-stage in the process sequence, a major part of the oxidation takes place without the recirculated products. This is advantageous because, among other reasons, substances are present in the recirculated products which decrease the activity of the catalyst. Lower temperatures can therefore be set, which increases the selectivity, but also leads to the fact that a lower amount of valuable steam at lower pressure is generated in the cooling system of the relevant oxidizers. The possibility of selecting the reaction temperature within limits ensures considerable flexibility for operating the plant. Depending on the economic circumstances—such as the requirement for higher-value steam, or the cost price of pX—the optimum oxidation temperature can be selected.

(2) If recirculated products are fed to a stage which is downstream in the process sequence of the first, preferably pX-rich stage, and in particular to the last stage, so that the concentration of the starting materials in the preceding stage or stages are not decreased by dilution, this downstream stage can be operated at temperatures <160° C. These temperatures, surprisingly, are completely sufficient for the oxidation of the readily oxidizable contents of the recirculated products.

(3) because of the high content of high-boiling pTA in the pX-rich stage, the temperature there can be increased, without having any fear of excessive product discharge together with the off-gas or foaming of the reaction mixture. This increases the space-time yield and generates higher-value steam. The higher temperature is, however, at the cost of the DMT yield. There is, in turn, as described under number (2), the possibility of matching the reaction temperature to the respective technical and economic circumstances.

(4) Since the pX oxidation in the pX-rich stage proceeds further than in comparable prior art processes, because of the comparatively low amounts of pTE fed, but which are sufficient for the handleability of the oxidized product, greater amounts of TPA are produced in this stage and, if appropriate, in downstream stages. As a result, the amount of recycled pTE can be decreased and energy can be saved in the crude ester distillation.

(5) The present invention can be used both in existing and in new plants, for example, in plants having two or more conventional vertical oxidizers arranged in series and in plants having horizontal oxidizers and subdivision into two or more chambers which correspond to the stages. Furthermore, it is possible to connect together, according to the present invention, oxidizers which are operated batchwise or in parallel. The present process is particularly applicable to DMT plants having three conventional vertical oxidizers arranged in series. It is immaterial whether the plants are operated with residue recirculation or thermolysis, with methanolysis and/or with isomer recirculation. Furthermore, it is inmmaterial whether DMT and/or pure terephthalic acid (PTA) is produced in the plants.

Process parameters pX is a conventional commercially available raw material which is available in >99% purity. The higher the degree of purity, the higher the price and the lower the amount of the resulting by-products, such as DMO and DMI. Since pX is expediently converted in one passage through the process only to an extent of 50 to 90%, recovered pX is used together with fresh pX. pTE originates from the crude ester distillation.

The oxygen-containing gases are generally air, which may be enriched with oxygen. Although this makes the reaction more vigorous and complicates the reaction procedure, the decreased amount of off-gas discharges fewer materials of value from the oxidation mixture, so that their recovery is less complex. The air is preferably used in a stoichiometric excess and is of an amount, and distributed to the stages in such a manner, that the off-gas from each stage contains approximately 2 to 5% by volume of oxygen.

The oxidation process comprises at least two stages. Preferably it comprises three, or even four or more, stages. In at least one stage, one of the above conditions (a) or (b) must be fulfilled. The other condition can, but need not be, fulfilled in the second stage. There are also operating states in which both conditions (a) and (b) are simultaneously fulfilled in one stage. In oxidation stages having three stages, again, in at least one stage, at least one of the conditions (a) or (b) must be fulfilled. The other condition can, but need not, be fulfilled in at least one further stage. In this case also, the concentrations of pX, pTE and pTA can simultaneously satisfy both conditions in one stage or more than one stage.

The oxidation mixture pTE content of 5 to 30% by mass in the at least one pX-rich stage and/or the pX content of 2 to 30% by mass, based on the sum of pTE and pTA, in the at least one pTE-rich stage are important features of the present process. The pTE concentration in the at least one pX-rich stage is preferably 5 to 20% by mass, more preferably 5 to 15% by mass, based on the total amount of oxidation mixture in the stage. The pX concentration in the at least one pTE-rich stage is preferably 5 to 20% by mass, and, more preferably, 5 to 15% by mass, based on the sum of the amounts of pTE and pTA in the stage.

The process according to the present invention uses a conventional catalyst used in the Witten-Hercules process. Therefore, inter alia, aqueous solutions containing 0.1 to 10% by mass of cobalt salts and manganese salts, with or without carboxylic acids, are used which are expediently extracted from the distillation residues produced in further stages of the DMT process and supplemented with fresh solution to compensate for the losses. Also, catalyst-containing recirculated residue streams can be added to the last stage(s) in the process sequence and extracted and/or fresh aqueous solution can be introduced solely into the preceding stage(s).

In principle, it is possible to introduce recirculated products having the noted oxidizable contents partly into a pX-rich and also into a pTE-rich stage. However, the recirculated products are preferably introduced into at least one stage which is arranged downstream of the first stage in the process sequence. Preferably, the recirculated products are introduced into the last stage in the process sequence. The recirculated products can also be introduced into an appropriate stage in a mixture with pTE.

The proportion of the pX which is oxidized in the at least one pX-rich stage can vary within broad limits. Generally, it is 25 to 75%, based on unreacted pX. However, it is preferred that pX is present in the pTE-rich stage in the concentration specified and thus sufficient for developing the advantageous H-donor action.

The temperature in the at least one pX-rich stage is generally 135° to 155° C., preferably 140° to 150° C. In the at least one pTE-rich stage, the temperature is generally 150° to 175° C., preferably 155° to 160° C. The oxidation takes place in all stages generally at pressures of 2 to 25 bar, preferably of 6 to 8 bar.

Plants for carrying out the process

Plants having three part-stages

Below is described the application of the present invention to the oxidation stage of a DMT plant having three conventional vertical oxidizers arranged in series which correspond to the three stages mentioned. This oxidation process is shown diagrammatically in FIG. 1. In this diagram the oxidizers 1 to 3 are of equal size. Alternatively, they can be of different sizes, which leads to different mean residence times.

The oxidizer 1, which corresponds to stage 1, has inlet lines for pX (1.1), pTE (1.2), catalyst solution (1.3), air (1.4) as oxygen-containing gas and any recirculated products (1.5). The air (1.4), here as also in the downstream oxidizers, is preferably distributed to inlet lines in the lower part of the oxidizer and in the upper part below the level of the liquid oxidation mixture.

The oxidation of pX and pTE is highly exothermic. The temperature in oxidizer 1, as in the downstream oxidizers, is kept at the desired value by means of heat exchangers (not shown in the figure). This temperature is sufficiently low that pX 1.1 does not boil at the prevailing pressure. The steam generated has a pressure of 1 to 8 bar, depending on the temperature.

Oxidation mixture 1.6 is conducted by means of pump 1.7 into oxidizer 2, which in turn is provided with inlet lines for pX (2.1), pTE (2.2), catalyst solution (2.3) and air (2.4). In addition, an inlet line for recirculated products (2.5) containing the oxidizable substances of value is present.

Oxidation mixture 2.6 is conveyed from oxidizer 2 by means of pump 2.7 into oxidizer 3, which, as in oxidizer 2, is provided with inlet lines for pX (3.1), pT E (3.2), catalyst solution (3.3), air (3.4) and recirculated products (3.5). The oxidation mixture (3.6) exits at the bottom of oxidizer 3 and can be further processed in a conventional manner. Low-oxygen off-gas 4 is taken off from the tops of the oxidizers and, after appropriate cleaning with recovery of any substances of value, is discharged to the atmosphere.

In a three-stage plant of this type, a pX-rich stage can be present, for example in oxidizer 1. The amount of pTE (1.2) is then dimensioned appropriately, i.e. is decreased with respect to conventional process procedures. It alone leads to a mode of operation according to the process of the invention, independently of the state of the concentration ratios in downstream oxidizers 2 and 3. For this, pTE (2.2) is introduced into oxidizer 2 in an amount which corresponds to the amount by which pTE (1.2) was reduced. The deficient pTE amount can also be distributed to the pTE inlet lines (2.2) and (3.2), but this is generally less preferred. In addition, recirculated products 2.5 can be introduced into oxidizer 2. These can be all of the recirculated products produced, or these can be distributed to inlet lines 2.5 and 3.5. However, it is preferred to feed all of the recirculated products to oxidizer 3 by inlet line 3.5. If desired, pX (2.1) can be introduced into oxidizers 2 and/or 3 in order to set the pX concentration according to the invention for at least one further pTE-rich stage in oxidizers 2 and/or 3. However, depending on the process parameters in the individual oxidizers and, in particular, in oxidizer 1, this concentration can occur even without further feed of pX.

Alternatively to the three-stage variant described, in which the first stage in the process sequence is a pX-rich stage, this first stage can also be a pTE-rich stage. Then, for example, pTE is fed via inlet line 1.2 and pX (1.1) is fed only in an amount such that the concentration according to the present invention for the pTE-rich stage prevails. The remaining major amounts of pX and pTE are distributed to inlet lines 2.1 and 2.2, respectively and/or 3.1 and 3.2, respectively, but are preferably fed solely via inlet line 3.1 and 3.2, respectively. The comments on the above process variant, in which the first stage in the process sequence is a pX-rich stage, also apply with regard to the recirculated products.

Plants having two part-stages

For plants of this type, the explanations of the three-stage embodiments likewise apply. Although with two oxidizers the plant is simpler and cheaper, it is also less flexible when optimization of process conditions is of interest. In one variant of the process having two stages, the first stage comprises two zones arranged in parallel, where, as in the process of JA62/14537 mentioned above, in one of these zones a molar excess of pX can prevail over pTE and, in the other zone, a molar excess of pTE can prevail over pX.

Figure 2:
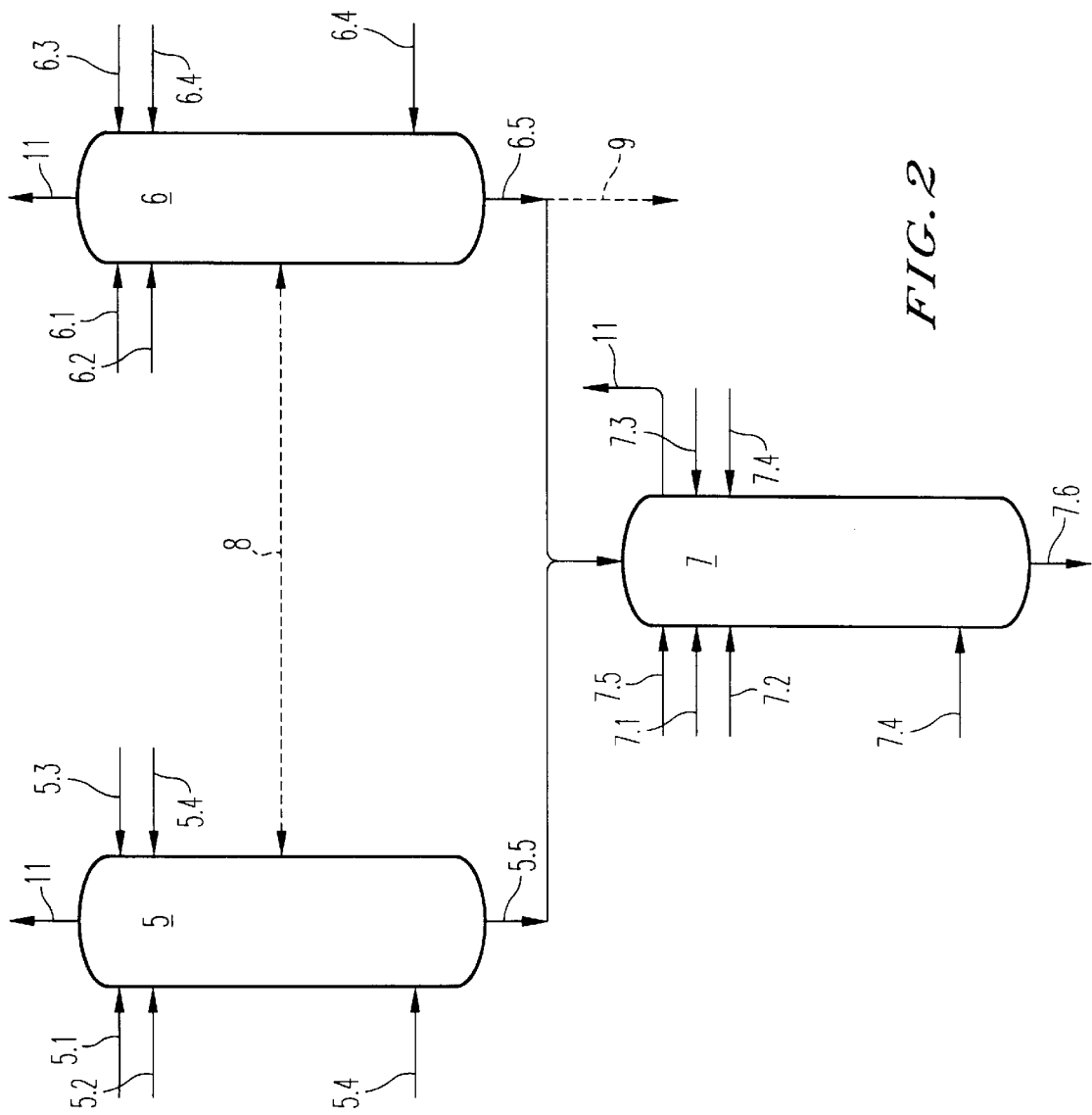
FIG. 2 is a diagram of a two-stage plant having three oxidizers, of which two oxidizers arranged in parallel form the first stage and the third oxidizer forms the second stage.

A corresponding plant having two oxidizers arranged in parallel for the first stage and a third oxidizer arranged in series for the second stage is shown diagrammatically in FIG. 2. Oxidizer 5 has feeds for pX (5.1), pTE (5.2), catalyst solution (5.3) and air (5.4), and also an outlet line for the oxidation mixture (5.5). Oxidizer 6 arranged in parallel also has corresponding feeds 6.1, 6.2, 6.3 and 6.4, and also corresponding outlet line 6.5. Oxidizers 5 and 6 are connected via line 8, through which the oxidation mixture can be exchanged between the oxidizers. Oxidation mixtures 5.5 and 6.5 are passed into oxidizer 7, which is provided with feed lines 7.1, 7.2, 7.3 and 7.4, in accordance with oxidizers 5 and 6. Furthermore, recirculated products 7.5 are fed to oxidizer 7 and oxidation mixture 7.6, which passes to esterification, is taken off from oxidizer 7. Via line 9, oxidation mixture 6.5 can be conducted directly to esterification, wholly or partially bypassing the oxidizer 7. Off-gas is taken off from the oxidizers via outlet lines 11, which off-gas is treated as described above.

In oxidizer 5, a molar excess of pX prevails over pTE, and in oxidizer 6 the reverse applies. Depending on the molar ratio, the conditions according to the present invention can be fulfilled in none, in one or in both, of the oxidizers 5 and 6. The latter case is a special case of the previously mentioned embodiment, in which both conditions (a) and (b) according to the present invention are fulfilled in one and the same stage. If conditions (a) and (b) according to the present invention do not prevail in either of oxidizers 5 and 6, care must be taken to ensure that the conditions in oxidizer 7 are according to the present invention, e.g. by feeding pX (7.1) and/or changing the ratio in which oxidation mixture 6.5 is distributed to oxidizer 7 and the esterification. Obviously, by means of suitable measures, the concentrations according to the present invention for the pTE-rich stage in the third oxidizer can be set even when the concentrations of pX and pTE already correspond to the conditions according to the present invention for a pX-rich stage in at least one of reactors 5 and 6.

Even though the invention has been explained for the special cases of oxidation using three conventional vertical oxidizers arranged in series and the two-stage oxidation using reactors arranged in parallel in the first stage, those skilled in the art will nevertheless see that the measures according to the invention can also be applied to other oxidations having a different number and/or arrangement of oxidizers, and/or can be applied to other types of oxidizers.

Having generally described this invention, a further understanding can be obtained by reference to certain specific examples which are provided herein for purposes of illustration only and are not intended to be limiting unless otherwise specified.

Examples

The following two examples compare the conventional mode of operation (6.1) and the mode of operation according to the present invention (6.2) of an oxidation plant having three part-stages, as shown in FIG. 1. In these examples, the same production rate of DMT was chosen as the basis for the mass balances given in the table. The catalyst streams are virtually identical in both cases and were not taken into account in the mass balances, since their amounts are very small.

Conventional mode of operation

In this case, all starting materials (pX, pTE, recirculated streams with or without oxidizable substances of value), except for air, were passed to oxidizer 1. The pX stream contained not only fresh pX, but also px-rich recirculated streams, which were produced as condensates of the oxidation off-gas and of the stripper vapors. These recirculated streams contained, inter alia, pTE in amounts such that its content in the pX stream was 12 to 20% by mass. The further recirculated streams (1.5) with or without oxidizable substances of value, originated from various downstream plant sections, such as crude ester distillation and methanolysis, and predominantly contained pTE and, inter alia, DMT, BME, HMBME, methyl methoxymethylbenzoate MMME), DM0, DMI and highboilers. All of the pTE and all pTE-containing streams were therefore introduced into oxidizer 1. As a result, the concentration of pTE in the oxidation mixture of oxidizer 1 was 35% by mass. In this mode of operation, the DMT yield, based on pX used, was about 88% of theory.

Mode of operation according to the present invention

In this case, the starting materials were not passed in total to oxidizer 1, but were distributed to the three oxidizers in accordance with the table. All of the pX was passed to oxidizer 1. It contained, as mentioned, pX-rich and also pTE-containing recirculated streams, so that the pTE content in oxidizer 1 was 15% by mass. The majority of pTE was introduced into oxidizer 2, with the remaining amount of pTE and the total amount of recirculated streams containing oxidizable and non-oxidizable substances of value being introduced into oxidizer 3. In this mode of operation, the DMT yield, based on pX used, was approximately 91% of theory.

TABLE

| Stream no. as in FIG. 1 | Example 6.1 Mass flow rate kg/h | Example 6.2 Mass flow rate kg/h |
|---|---|---|
| 1.1 | 35,000 | 34,000 |
| 1.2 | 22,400 | — |
| 1.4 | 28,066 | 32,840 |
| 1.5 | 12,600 | — |
| 1.6 | 68,032 | 32,545 |
| 2.2 | — | 20,400 |
| 2.4 | 29,516 | 28,644 |
| 2.6 | 67,518 | 52,996 |
| 3.2 | — | 2,000 |
| 3.4 | 18,961 | 14,399 |
| 3.5 | — | 12,600 |
| 3.6 | 68,599 | 67,918 |
| 4 | 77,944 | 76,905 |

This application is based on German Patent Application 196 41 912.3, filed with the German Patent Office on Oct. 11, 1996, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for oxidation of p-xylene and methyl p-toluate comprising oxidizing p-xylene and methyl p-toluate with oxygen containing gases in at least two sequential stages in the presence of a catalyst, wherein said at least two sequential stages comprise at least one p-xylene rich stage and at least one methyl p-toluate rich stage, wherein at least one of the following steps (a) and (b) occurs:

(a) in said at least one p-xylene rich stage at least a portion of p-xylene present is oxidized in the presence of 5 to 30% by mass of methyl p-toluate, based on a total amount of oxidation mixture in said at least one p-xylene rich stage; or (b) in said methyl p-toluate rich stage at least one of methyl p-toluate or p-toluic acid is oxidized in the presence of 2 to 30% by mass of p-xylene, based on a total amount of methyl p-toluate and p-toluic acid in said methyl p-toluate rich stage.

2. The process as claimed in claim 1, wherein the methyl p-toluate is present in the p-xylene rich stage in an amount of 5 to 15% by mass, based on the total amount of the oxidation mixture in the p-xylene rich stage.

3. The process as claimed claim 1, wherein the p-xylene is present in the methyl p-toluate rich stage in an amount of 5 to 15% by mass, based on the total amount of methyl p-toluate and p-toluic acid in the methyl p-toluate rich stage.

4. The process as claimed in claim 1, wherein the p-xylene rich stage is upstream of the methyl p-toluate rich stage.

5. The process as claimed in claim 1, wherein the methyl p-toluate rich stage is upstream of the p-xylene rich stage.

6. The process as claimed in claim 1, wherein recirculated products are introduced into at least one of said sequential stages, so long said at least one of said sequential stages is not a first stage in the oxidation process.

7. The process as claimed in claim 6, wherein the recirculated products are introduced into a last stage of the oxidation process.

8. The process as claimed in claim 1, wherein the oxidation process comprises two stages, wherein a first stage is the p-xylene rich stage and a second stage is the methyl p-toluate rich stage.

9. The process as claimed in claim 1, wherein the oxidation process comprises two stages, wherein a first stage is the methyl p-toluate rich stage and a second stage is the p-xylene-rich stage.

10. The process as claimed in claim 8, wherein the first stage comprises two oxidation zones arranged in parallel, wherein one of the oxidation zones is a p-xylene rich oxidation zone containing a molar excess of p-xylene over methyl p-toluate, and the other of the oxidation zones is a methyl p-toluate rich oxidation zone containing a molar excess of methyl p-toluate over p-xylene.

11. The process as claimed in claim 10, wherein, prior to transfer to the second stage, a portion of an oxidation mixture from the first stage is passed from one of the oxidation zones to the other.

12. The process as claimed in claim 10, farther comprising an esterification stage, wherein a portion of an oxidation mixture from the methyl p-toluate rich oxidation zone is passed directly into the esterification stage following oxidation.

13. The process as claimed in claim 1, wherein the oxidation process comprises three stages, wherein a first stage is the p-xylene-rich stage and a third stage is the methyl p-toluate rich stage.

14. The process as claimed in claim 1, wherein the oxidation process comprises three stages, wherein a first stage is the methyl p-toluate rich stage and a third stage is the p-xylene rich stage.

15. The process as claimed in claim 1, wherein each of conditions (a) and (b) are met in a single stage.

* * * * *